(12) United States Patent
Bayer et al.

(10) Patent No.: US 8,310,530 B2
(45) Date of Patent: Nov. 13, 2012

(54) DEVICE AND METHOD FOR REDUCING EFFECTS OF VIDEO ARTIFACTS

(75) Inventors: Lex Bayer, Palo Alto, CA (US); Robert Okas, Menlo Park, CA (US); Peter C. Okas, legal representative, Atascadero, CA (US); Alex Niel, Daly City, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 1328 days.

(21) Appl. No.: 11/751,597

(22) Filed: May 21, 2007

(65) Prior Publication Data
US 2007/0279486 A1    Dec. 6, 2007

Related U.S. Application Data

(60) Provisional application No. 60/801,748, filed on May 19, 2006.

(51) Int. Cl.
*A62B 1/04*    (2006.01)
(52) U.S. Cl. .............................. 348/65; 348/72
(58) Field of Classification Search .................. 348/65, 348/72
See application file for complete search history.

(56) References Cited

U.S. PATENT DOCUMENTS

| | | | |
|---|---|---|---|
| 3,437,747 A | 4/1969 | Sheldon | |
| 3,610,231 A | 10/1971 | Takahashi et al. | |
| 3,643,653 A | 2/1972 | Takahashi et al. | |
| 3,739,770 A | 6/1973 | Mori | |
| 3,889,662 A | 6/1975 | Mitsui | |
| 3,897,775 A | 8/1975 | Furihata | |
| 3,918,438 A | 11/1975 | Hayamizu et al. | |
| 4,261,344 A | 4/1981 | Moore et al. | |
| 4,351,587 A | 9/1982 | Matsuo et al. | |
| 4,398,811 A | 8/1983 | Nishioka et al. | |
| 4,494,549 A | 1/1985 | Namba et al. | |
| 4,573,450 A | 3/1986 | Arakawa | |
| 4,586,491 A | 5/1986 | Carpenter | |
| 4,625,236 A | 11/1986 | Fujimori et al. | |
| 4,646,722 A | 3/1987 | Silverstein et al. | |
| 4,699,463 A | 10/1987 | D'Amelio et al. | |
| 4,721,097 A | 1/1988 | D'Amelio | |

(Continued)

FOREIGN PATENT DOCUMENTS

CN    1 628 603    6/2005

(Continued)

OTHER PUBLICATIONS

U.S. Appl. No. 11/153,007, filed Jun. 14, 2005, Seddiqui et al.

(Continued)

*Primary Examiner* — Firmin Backer
*Assistant Examiner* — Jonathan Bui
(74) *Attorney, Agent, or Firm* — Morrison & Foerster LLP

(57) ABSTRACT

A method for reducing an effect of a video artifact includes adjusting a phase of a second imaging device's video clock signal so that a phase of the second imaging device's video synchronization signal matches a phase of a first imaging device's video synchronization signal. An endoscopic system includes a first imaging device, a second imaging device, a light source, and a controller that reduces an artifact in an image produced by the first imaging device. In some embodiments, the first imaging device faces the light source.

30 Claims, 5 Drawing Sheets

U.S. PATENT DOCUMENTS

| | | | |
|---|---|---|---|
| 4,727,859 A | 3/1988 | Lia | |
| 4,741,326 A | 5/1988 | Sidall et al. | |
| 4,790,295 A | 12/1988 | Tashiro | |
| 4,800,870 A | 1/1989 | Reid, Jr. | |
| 4,825,850 A | 5/1989 | Opie et al. | |
| 4,836,211 A | 6/1989 | Sekino et al. | |
| 4,846,154 A | 7/1989 | MacAnally et al. | |
| 4,852,551 A | 8/1989 | Opie et al. | |
| 4,853,773 A | 8/1989 | Hibino et al. | |
| 4,862,873 A | 9/1989 | Yajima et al. | |
| 4,867,138 A | 9/1989 | Kubota et al. | |
| 4,869,238 A | 9/1989 | Opie et al. | |
| 4,870,488 A | 9/1989 | Ikuno et al. | |
| 4,873,572 A | 10/1989 | Miyazaki et al. | |
| 4,873,965 A | 10/1989 | Danieli | |
| 4,884,133 A | 11/1989 | Kanno et al. | |
| 4,899,732 A | 2/1990 | Cohen | |
| 4,905,667 A | 3/1990 | Foerster et al. | |
| 4,907,395 A | 3/1990 | Opie et al. | |
| 4,911,148 A | 3/1990 | Sosnowski et al. | |
| 4,911,564 A | 3/1990 | Baker | |
| 4,926,258 A | 5/1990 | Sasaki | |
| 4,947,827 A | 8/1990 | Opie et al. | |
| 4,947,828 A | 8/1990 | Carpenter et al. | |
| 4,979,496 A | 12/1990 | Komi | |
| 4,991,565 A | 2/1991 | Takahashi et al. | |
| 5,019,040 A | 5/1991 | Itaoka et al. | |
| 5,025,778 A | 6/1991 | Silverstein et al. | |
| 5,026,377 A | 6/1991 | Burton et al. | |
| 5,050,585 A | 9/1991 | Takahashi | |
| RE34,100 E | 10/1992 | Opie et al. | |
| RE34,110 E | 10/1992 | Opie et al. | |
| 5,159,446 A | 10/1992 | Hibino et al. | |
| 5,166,787 A | 11/1992 | Irion | |
| 5,178,130 A | 1/1993 | Kaiya et al. | |
| 5,187,572 A | 2/1993 | Nakamura et al. | |
| 5,193,525 A | 3/1993 | Silverstein et al. | |
| 5,196,928 A | 3/1993 | Karasawa et al. | |
| 5,253,638 A | 10/1993 | Tamburrino et al. | |
| 5,260,780 A | 11/1993 | Staudt, III | |
| 5,271,381 A | 12/1993 | Ailinger et al. | |
| 5,305,121 A | 4/1994 | Moll | |
| 5,318,031 A | 6/1994 | Mountford et al. | |
| 5,329,887 A | 7/1994 | Ailinger et al. | |
| 5,337,734 A | 8/1994 | Saab | |
| 5,381,784 A | 1/1995 | Adair | |
| 5,398,685 A | 3/1995 | Wilk et al. | |
| 5,406,938 A | 4/1995 | Mersch et al. | |
| 5,434,669 A * | 7/1995 | Tabata et al. | 356/477 |
| 5,443,781 A | 8/1995 | Saab | |
| 5,447,148 A | 9/1995 | Oneda et al. | |
| 5,483,951 A | 1/1996 | Frassica et al. | |
| 5,494,483 A | 2/1996 | Adair | |
| 5,518,501 A | 5/1996 | Oneda et al. | |
| 5,520,607 A | 5/1996 | Frassica et al. | |
| 5,530,238 A | 6/1996 | Meulenbrugge et al. | |
| 5,533,496 A | 7/1996 | De Faria-Correa et al. | |
| 5,536,236 A | 7/1996 | Yabe et al. | |
| 5,556,367 A | 9/1996 | Yabe et al. | |
| 5,613,936 A | 3/1997 | Czarnek et al. | |
| 5,614,943 A | 3/1997 | Nakamura et al. | |
| 5,626,553 A | 5/1997 | Frassica et al. | |
| 5,634,466 A | 6/1997 | Gruner | |
| 5,653,677 A | 8/1997 | Okada et al. | |
| 5,667,476 A | 9/1997 | Frassica et al. | |
| 5,679,216 A | 10/1997 | Takayama et al. | |
| 5,681,260 A | 10/1997 | Ueda et al. | |
| 5,682,199 A | 10/1997 | Lankford | |
| 5,685,822 A | 11/1997 | Harhen | |
| 5,692,729 A | 12/1997 | Harhen | |
| 5,696,850 A | 12/1997 | Parulski et al. | |
| 5,702,348 A | 12/1997 | Harhen | |
| 5,706,128 A | 1/1998 | Greenberg | |
| 5,711,299 A | 1/1998 | Manwaring et al. | |
| 5,722,933 A | 3/1998 | Yabe et al. | |
| 5,752,912 A | 5/1998 | Takahashi et al. | |
| 5,762,603 A | 6/1998 | Thompson | |
| 5,817,061 A | 10/1998 | Goodwin et al. | |
| 5,827,177 A | 10/1998 | Oneda et al. | |
| 5,833,603 A | 11/1998 | Kovacs et al. | |
| 5,843,103 A | 12/1998 | Wulfman | |
| 5,843,460 A | 12/1998 | Labigne et al. | |
| 5,860,914 A | 1/1999 | Chiba et al. | |
| 5,876,329 A | 3/1999 | Harhen | |
| 5,916,147 A | 6/1999 | Boury | |
| 5,924,977 A | 7/1999 | Yabe et al. | |
| 5,938,587 A | 8/1999 | Taylor et al. | |
| 5,982,932 A * | 11/1999 | Prokoski | 382/224 |
| 5,989,182 A | 11/1999 | Hori et al. | |
| 5,989,224 A | 11/1999 | Exline et al. | |
| 6,017,358 A | 1/2000 | Yoon | |
| 6,026,323 A | 2/2000 | Skladnev et al. | |
| 6,066,090 A | 5/2000 | Yoon | |
| 6,099,464 A | 8/2000 | Shimizu et al. | |
| 6,099,466 A | 8/2000 | Sano et al. | |
| 6,099,485 A | 8/2000 | Patterson | |
| 6,106,463 A | 8/2000 | Wilk | |
| 6,174,280 B1 | 1/2001 | Oneda et al. | |
| 6,190,330 B1 | 2/2001 | Harhen | |
| 6,214,028 B1 | 4/2001 | Yoon et al. | |
| 6,261,226 B1 | 7/2001 | McKenna et al. | |
| 6,261,307 B1 | 7/2001 | Yoon et al. | |
| 6,277,064 B1 | 8/2001 | Yoon | |
| 6,296,608 B1 | 10/2001 | Daniels et al. | |
| 6,301,047 B1 | 10/2001 | Hoshino et al. | |
| 6,350,231 B1 | 2/2002 | Ailinger et al. | |
| 6,369,855 B1 * | 4/2002 | Chauvel et al. | 348/423.1 |
| 6,375,653 B1 | 4/2002 | Desai | |
| 6,387,043 B1 | 5/2002 | Yoon | |
| 6,433,492 B1 * | 8/2002 | Buonavita | 315/248 |
| 6,456,684 B1 | 9/2002 | Mun et al. | |
| 6,461,294 B1 | 10/2002 | Oneda et al. | |
| 6,482,149 B1 | 11/2002 | Torii | |
| 6,527,704 B1 | 3/2003 | Chang et al. | |
| 6,547,724 B1 | 4/2003 | Soble et al. | |
| 6,554,767 B2 | 4/2003 | Tanaka | |
| 6,564,088 B1 | 5/2003 | Soller et al. | |
| 6,640,017 B1 | 10/2003 | Tsai et al. | |
| 6,648,816 B2 | 11/2003 | Irion et al. | |
| 6,683,716 B1 | 1/2004 | Costales | |
| 6,687,010 B1 | 2/2004 | Horii et al. | |
| 6,697,536 B1 | 2/2004 | Yamada | |
| 6,699,180 B2 | 3/2004 | Kobayashi | |
| 6,736,773 B2 | 5/2004 | Wendlandt et al. | |
| 6,748,975 B2 | 6/2004 | Hartshorne et al. | |
| 6,796,939 B1 | 9/2004 | Hirata et al. | |
| 6,833,871 B1 | 12/2004 | Merrill et al. | |
| 6,845,190 B1 | 1/2005 | Smithwick et al. | |
| 6,891,977 B2 | 5/2005 | Gallagher | |
| 6,916,286 B2 | 7/2005 | Kazakevich | |
| 6,928,314 B1 | 8/2005 | Johnson et al. | |
| 6,929,636 B1 | 8/2005 | von Alten | |
| 6,947,784 B2 | 9/2005 | Zalis | |
| 6,951,536 B2 | 10/2005 | Yokoi et al. | |
| 6,965,702 B2 | 11/2005 | Gallagher | |
| 6,966,906 B2 | 11/2005 | Brown | |
| 6,974,240 B2 * | 12/2005 | Takahashi | 362/574 |
| 6,974,411 B2 | 12/2005 | Belson | |
| 6,997,871 B2 | 2/2006 | Sonnenschein et al. | |
| 7,004,900 B2 | 2/2006 | Wendlandt et al. | |
| 7,029,435 B2 | 4/2006 | Nakao | |
| 7,041,050 B1 | 5/2006 | Ronald | |
| 7,095,548 B1 * | 8/2006 | Cho et al. | 359/298 |
| 7,103,228 B2 | 9/2006 | Kraft et al. | |
| 7,116,352 B2 * | 10/2006 | Yaron | 348/45 |
| 7,173,656 B1 | 2/2007 | Dunton et al. | |
| 7,228,004 B2 | 6/2007 | Gallagher et al. | |
| 7,280,141 B1 | 10/2007 | Frank et al. | |
| 7,317,458 B2 | 1/2008 | Wada | |
| 7,322,934 B2 | 1/2008 | Miyake et al. | |
| 7,341,555 B2 | 3/2008 | Ootawara et al. | |
| 7,362,911 B1 | 4/2008 | Frank | |
| 7,389,892 B2 | 6/2008 | Park | |
| 7,405,877 B1 | 7/2008 | Schechterman | |
| 7,435,218 B2 | 10/2008 | Krattiger et al. | |
| 7,436,562 B2 | 10/2008 | Nagasawa et al. | |
| 7,507,200 B2 | 3/2009 | Okada | |

| | | |
|---|---|---|
| 7,551,196 B2 * | 6/2009 | Ono et al. ............... 348/65 |
| 7,556,599 B2 | 7/2009 | Rovegno |
| 7,561,190 B2 * | 7/2009 | Deng et al. ............... 348/226.1 |
| 7,621,869 B2 | 11/2009 | Ratnakar |
| 7,646,520 B2 | 1/2010 | Funaki et al. |
| 7,678,043 B2 | 3/2010 | Gilad |
| 7,683,926 B2 * | 3/2010 | Schechterman et al. ...... 348/42 |
| 7,749,156 B2 | 7/2010 | Ouchi |
| 7,825,964 B2 | 11/2010 | Hoshino et al. |
| 7,864,215 B2 | 1/2011 | Carlsson et al. |
| 7,910,295 B2 | 3/2011 | Hoon et al. |
| 7,927,272 B2 | 4/2011 | Bayer et al. |
| 8,009,167 B2 | 8/2011 | Dekel et al. |
| 8,064,666 B2 | 11/2011 | Bayer |
| 8,070,743 B2 | 12/2011 | Kagan et al. |
| 2001/0007468 A1 | 7/2001 | Sugimoto et al. |
| 2001/0037052 A1 * | 11/2001 | Higuchi et al. ............... 600/178 |
| 2001/0051766 A1 | 12/2001 | Gazdinski |
| 2001/0056238 A1 | 12/2001 | Tsujita |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1 | 7/2002 | Griego et al. |
| 2002/0099267 A1 | 7/2002 | Wendlandt et al. |
| 2002/0101546 A1 | 8/2002 | Sharp et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0193662 A1 | 12/2002 | Belson |
| 2003/0004399 A1 | 1/2003 | Belson |
| 2003/0011768 A1 | 1/2003 | Jung et al. |
| 2003/0032863 A1 | 2/2003 | Kazakevich |
| 2003/0040668 A1 | 2/2003 | Kaneko et al. |
| 2003/0045778 A1 | 3/2003 | Ohline et al. |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0125788 A1 | 7/2003 | Long |
| 2003/0130711 A1 | 7/2003 | Pearson et al. |
| 2003/0153866 A1 | 8/2003 | Long et al. |
| 2003/0161545 A1 | 8/2003 | Gallagher |
| 2003/0167007 A1 | 9/2003 | Belson |
| 2003/0171650 A1 | 9/2003 | Tartaglia et al. |
| 2003/0176767 A1 | 9/2003 | Long et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197781 A1 | 10/2003 | Sugimoto et al. |
| 2003/0197793 A1 | 10/2003 | Mitsunaga et al. |
| 2003/0216727 A1 | 11/2003 | Long |
| 2003/0225433 A1 | 12/2003 | Nakao |
| 2003/0233115 A1 | 12/2003 | Eversull et al. |
| 2004/0023397 A1 * | 2/2004 | Vig et al. ............... 436/1 |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0097790 A1 | 5/2004 | Farkas et al. |
| 2004/0109164 A1 * | 6/2004 | Horii et al. ............... 356/479 |
| 2004/0109319 A1 * | 6/2004 | Takahashi ............... 362/321 |
| 2004/0111019 A1 | 6/2004 | Long |
| 2004/0122291 A1 * | 6/2004 | Takahashi ............... 600/180 |
| 2004/0141054 A1 | 7/2004 | Mochida et al. |
| 2004/0158124 A1 | 8/2004 | Okada |
| 2004/0207618 A1 * | 10/2004 | Williams et al. ............ 345/212 |
| 2004/0242987 A1 | 12/2004 | Liew et al. |
| 2005/0010084 A1 | 1/2005 | Tsai |
| 2005/0014996 A1 | 1/2005 | Konomura et al. |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser et al. |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 | 8/2005 | Mackin |
| 2005/0203420 A1 | 9/2005 | Kleen et al. |
| 2005/0215911 A1 * | 9/2005 | Alfano et al. ............... 600/476 |
| 2005/0222500 A1 | 10/2005 | Itoi |
| 2005/0228224 A1 | 10/2005 | Okada et al. |
| 2005/0267361 A1 | 12/2005 | Younker et al. |
| 2005/0272975 A1 | 12/2005 | McWeeney et al. |
| 2005/0272977 A1 | 12/2005 | Saadat et al. |
| 2006/0044267 A1 | 3/2006 | Xie et al. |
| 2006/0052709 A1 | 3/2006 | DeBaryshe et al. |
| 2006/0058584 A1 | 3/2006 | Hirata |
| 2006/0106286 A1 | 5/2006 | Wendlandt et al. |
| 2006/0149127 A1 | 7/2006 | Seddiqui et al. |
| 2006/0149129 A1 | 7/2006 | Watts et al. |
| 2006/0183975 A1 | 8/2006 | Saadat et al. |
| 2006/0184037 A1 * | 8/2006 | Ince et al. ............... 600/476 |
| 2006/0217594 A1 | 9/2006 | Ferguson |
| 2006/0279632 A1 | 12/2006 | Anderson |
| 2006/0285766 A1 | 12/2006 | Ali |
| 2006/0293562 A1 | 12/2006 | Uchimura et al. |
| 2007/0015967 A1 | 1/2007 | Boulais et al. |
| 2007/0015989 A1 | 1/2007 | Desai et al. |
| 2007/0083081 A1 | 4/2007 | Schlagenhauf et al. |
| 2007/0103460 A1 | 5/2007 | Zhang et al. |
| 2007/0142711 A1 | 6/2007 | Bayer et al. |
| 2007/0173686 A1 | 7/2007 | Lin et al. |
| 2007/0177008 A1 | 8/2007 | Bayer et al. |
| 2007/0177009 A1 | 8/2007 | Bayer et al. |
| 2007/0183685 A1 | 8/2007 | Wada et al. |
| 2007/0185384 A1 | 8/2007 | Bayer et al. |
| 2007/0225552 A1 | 9/2007 | Segawa et al. |
| 2007/0225734 A1 | 9/2007 | Bell et al. |
| 2007/0238927 A1 | 10/2007 | Ueno et al. |
| 2007/0244354 A1 | 10/2007 | Bayer |
| 2007/0270642 A1 | 11/2007 | Bayer et al. |
| 2007/0279486 A1 | 12/2007 | Bayer et al. |
| 2007/0280669 A1 | 12/2007 | Karim |
| 2007/0293720 A1 | 12/2007 | Bayer |
| 2008/0021269 A1 | 1/2008 | Tinkham et al. |
| 2008/0021274 A1 | 1/2008 | Bayer et al. |
| 2008/0033450 A1 | 2/2008 | Bayer et al. |
| 2008/0039693 A1 | 2/2008 | Karasawa |
| 2008/0064931 A1 | 3/2008 | Schena et al. |
| 2008/0065110 A1 | 3/2008 | Duval et al. |
| 2008/0071291 A1 | 3/2008 | Duval et al. |
| 2008/0079827 A1 | 4/2008 | Hoshino et al. |
| 2008/0097292 A1 | 4/2008 | Cabiri et al. |
| 2008/0114288 A1 | 5/2008 | Whayne et al. |
| 2008/0130108 A1 | 6/2008 | Bayer et al. |
| 2008/0154288 A1 | 6/2008 | Belson |
| 2008/0199829 A1 | 8/2008 | Paley et al. |
| 2008/0275298 A1 | 11/2008 | Ratnakar |
| 2009/0015842 A1 * | 1/2009 | Leitgeb et al. ............... 356/456 |
| 2009/0023998 A1 | 1/2009 | Ratnakar |
| 2009/0028407 A1 * | 1/2009 | Seibel et al. ............... 382/131 |
| 2009/0036739 A1 | 2/2009 | Hadani |
| 2009/0049627 A1 | 2/2009 | Kritzler |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0213211 A1 | 8/2009 | Bayer et al. |
| 2009/0231419 A1 | 9/2009 | Bayer |
| 2010/0217076 A1 | 8/2010 | Ratnakar |
| 2011/0160535 A1 | 6/2011 | Bayer et al. |
| 2011/0213206 A1 | 9/2011 | Boutillette et al. |

FOREIGN PATENT DOCUMENTS

| | | |
|---|---|---|
| CN | 1628603 A | 6/2005 |
| DE | 196 26 433 | 1/1998 |
| DE | 20 2006 017 173 U1 | 3/2007 |
| EP | 0 586 162 | 3/1994 |
| EP | 1 570 778 | 9/2005 |
| EP | 1 769 720 A1 | 4/2007 |
| FR | 711 949 | 9/1931 |

| | | |
|---|---|---|
| JP | 49-130235 A | 12/1974 |
| JP | 56-9712 A | 1/1981 |
| JP | 56-56486 | 5/1981 |
| JP | 60-83636 A | 5/1985 |
| JP | 60-111217 A | 6/1985 |
| JP | 62-094312 U1 | 6/1987 |
| JP | 63-309912 A | 12/1988 |
| JP | 1-267514 A | 10/1989 |
| JP | 1-172847 U | 12/1989 |
| JP | 2-295530 A | 12/1990 |
| JP | 3-159629 A | 7/1991 |
| JP | 4-500768 A | 2/1992 |
| JP | 5-285091 A | 11/1993 |
| JP | 5-307144 A | 11/1993 |
| JP | 5-341210 A | 12/1993 |
| JP | 60-76714 A | 3/1994 |
| JP | 6-130308 A | 5/1994 |
| JP | 6-169880 A | 6/1994 |
| JP | 7-352 A | 1/1995 |
| JP | 7-354 A | 1/1995 |
| JP | 7-021001 U | 4/1995 |
| JP | 8-206061 A | 8/1996 |
| JP | 7-136108 A | 5/1998 |
| JP | 11-76150 A | 3/1999 |
| JP | 2003-220023 A | 8/2003 |
| JP | 2004-202252 A | 7/2004 |
| JP | 2004-525717 A | 8/2004 |
| JP | 2004-537362 A | 12/2004 |
| JP | 2007-143580 A | 6/2007 |
| WO | WO 93/15648 | 8/1993 |
| WO | WO-99/17542 A1 | 4/1999 |
| WO | WO-99/30506 A1 | 6/1999 |
| WO | WO 02/085194 | 10/2002 |
| WO | WO-02/094105 A2 | 11/2002 |
| WO | WO-02/094105 A3 | 11/2002 |
| WO | WO-03/013349 A2 | 2/2003 |
| WO | WO-03/013349 A3 | 2/2003 |
| WO | WO-2006/073676 A1 | 7/2006 |
| WO | WO-2006/073725 A1 | 7/2006 |
| WO | WO-2006/110275 A2 | 10/2006 |
| WO | WO-2006/110275 A3 | 10/2006 |
| WO | WO-2007/015241 A2 | 2/2007 |
| WO | WO-2007/015241 A3 | 2/2007 |
| WO | WO-2007/070644 A2 | 6/2007 |
| WO | WO-2007/070644 A3 | 6/2007 |
| WO | WO-2007/087421 A2 | 8/2007 |
| WO | WO-2007/087421 A3 | 8/2007 |
| WO | WO-2007/092533 A2 | 8/2007 |
| WO | WO-2007/092533 A3 | 8/2007 |
| WO | WO-2007/092636 A2 | 8/2007 |
| WO | WO-2007/092636 A3 | 8/2007 |
| WO | WO-2007/136859 A2 | 11/2007 |
| WO | WO-2007/136859 A3 | 11/2007 |
| WO | WO-2007/136879 A2 | 11/2007 |
| WO | WO-2007/136879 A3 | 11/2007 |
| WO | WO-2007/136879 B1 | 11/2007 |
| WO | WO-2009/014895 A1 | 1/2009 |
| WO | WO-2009/015396 A2 | 1/2009 |
| WO | WO-2009/015396 A3 | 1/2009 |
| WO | WO-2009/049322 A2 | 4/2009 |
| WO | WO-2009/049322 A3 | 4/2009 |
| WO | WO-2009/062179 A1 | 5/2009 |

OTHER PUBLICATIONS

U.S. Appl. No. 11/160,646, filed Jul. 1, 2005, Desai et al.
U.S. Appl. No. 11/215,660, filed Aug. 29, 2005, Watts et al.
U.S. Appl. No. 11/609,838, filed Dec. 12, 2006, Bayer et al.
U.S. Appl. No. 11/626,189, filed Jan. 23, 2007, Bayer et al.
U.S. Appl. No. 11/673,470, filed Feb. 9, 2007, Bayer et al.
U.S. Appl. No. 11/672,020, filed Feb. 6, 2007, Bayer et al.
U.S. Appl. No. 11/736,438, filed Apr. 17, 2007, Bayer.
U.S. Appl. No. 11/751,596, filed May 21, 2007, Bayer.
U.S. Appl. No. 11/751,605, filed May 21, 2007, Diel et al.
U.S. Appl. No. 11/828,835, filed Jul. 26, 2007, Bayer.
U.S. Appl. No. 11/834,540, filed Aug. 6, 2007, Bayer.
International Search Report for PCT/US2005/044624, filed Dec. 8, 2005, mailed May 19, 2006, 16 pgs.
International Search Report for PCT/US2006/047748, filed Dec. 13, 2006, mailed Jun. 20, 2007, 12 pgs.
Invitation to Pay Additional Fees for PCT/US2007/002096, filed Jan. 23, 2007, mailed Jul. 6, 2007, 4 pgs.
Invitation to Pay Additional Fees for PCT/US2007/003631, filed Feb. 9, 2007, mailed Aug. 7, 2007, 5 pgs.
Invitation to Pay Additional Fees for PCT/US2007/003322, filed Feb. 6, 2007, mailed Aug. 7, 2007, 6 pgs.
International Search Report for PCT/US2008/069435, filed Jul. 8, 2008, mailed Oct. 23, 2008, 8 pgs.
Invitation to Pay Additional Fees for PCT/US2008/071390, filed Jul. 28, 2008, mailed Nov. 11, 2008, 5 pgs.
International Search Report for PCT/US2007/012358 filed May 21, 2007, mailed Dec. 11, 2007, 6 pgs.
Advisory Action mailed on Nov. 2, 2010, for U.S. Appl. No. 11/609,838, filed Dec. 12, 2006, 3 pages.
Advisory Action mailed on May 23, 2011, for U.S. Appl. No. 11/751,605, filed May 21, 2007, 3 pages.
Amendment in Response to Non-Final Office Action filed on Jun. 29, 2009, for U.S. Appl. No. 11/215,660, filed Aug. 29, 2005, 9 pages.
Amendment in Response to Final Office Action filed on Mar. 8, 2010, for U.S. Appl. No. 11/215,660, filed Aug. 29, 2005, 11 pages.
Amendment in Response to Non-Final Office Action filed on Jun. 25, 2010, for U.S. Appl. No. 11/609,838, filed Dec. 12, 2006, 14 pages.
Amendment in Response to Non-Final Office Action filed on Aug. 30, 2010, for U.S. Appl. No. 11/215,660, filed Aug. 29, 2005, 17 pages.
Amendment in Response to Final Office Action filed on Oct. 22, 2010, for U.S. Appl. No. 11/609,838, filed Dec. 12, 2006, 15 pages.
Amendment in Response to Non-Final Office Action filed on Oct. 22, 2010, for U.S. Appl. No. 11/834,540, filed Aug. 6, 2007, 13 pages.
Amendment in Response to Non-Final Office Action filed on Feb. 9, 2011, for U.S. Appl. No. 11/828,835, filed Jul. 26, 2007, 10 pages.
Amendment in Response to Non-Final Office Action filed on Feb. 25, 2011, for U.S. Appl. No. 11/751,605, filed May 21, 2007, 15 pages.
Amendment in Response to Final Office Action filed on Feb. 28, 2011, for U.S. Appl. No. 11/215,660, filed Aug. 29, 2005, 11 pages.
Amendment in Response to Non-Final Office Action filed on Apr. 12, 2011, for U.S. Appl. No. 11/626,189, filed Jan. 23, 2007, 18 pages.
Amendment in Response to Non-Final Office Action filed on May 17, 2011, for U.S. Appl. No. 11/609,838, filed Dec. 12, 2006, 18 pages.
Amendment in Response to Final Office Action filed on May 17, 2011, for U.S. Appl. No. 11/751,605, filed May 21, 2007, 10 pages.
Amendment in Response to Final Office Action filed on May 24, 2011, for U.S. Appl. No. 11/828,835, filed Jul. 26, 2007, 13 pages.
Amendment in Response to Non-Final Office Action filed on May 24, 2011, for U.S. Appl. No. 11/736,438, filed Apr. 17, 2007, 11 pages.
Amendment in Response to Non-Final Office Action filed on Jun. 6, 2011, for U.S. Appl. No. 12/101,050, filed Apr. 10, 2008, 17 pages.
Amendment in response to Final Office Action filed on Jun. 7, 2011, for U.S. Appl. No. 11/751,605, filed May 21, 2007, 11 pages.
Amendment in Response to Final Office Action filed on Dec. 7, 2011, for U.S. Appl. No. 11/736,438, filed Apr. 17, 2007, 10 pages.
Amendment in Response to Non-Final Office Action filed on Jan. 9, 2012, for U.S. Appl. No. 11/751,596, filed May 21, 2007, 9 pages.
Amendment in Response to Non-Final Office Action filed on Feb. 15, 2012, for U.S. Appl. No. 11/626,189, filed Jan. 23, 2007, 13 pages.
European Communication mailed on Jan. 22, 2009, for European Application No. 07777255.6, filed on May 21, 2007, 2 pages.
European Office Action mailed on May 5, 2009, for European Patent Application No. 07763368.3, filed on Feb. 6, 2007, 3 pages.
European Office Action mailed on Feb. 5, 2010, for European Patent Application No. 06845440.4, filed on Dec. 13, 2006, 4 pages.
European Office Action mailed on Apr. 1, 2010, for European Patent Application No. 07717235.1, filed on Feb. 9, 2007, 2 pages.
European Office Action mailed on Nov. 8, 2010, for European Patent Application No. 05854262.2, filed on Dec. 8, 2005, 5 pages.
European Office Action mailed on Jun. 14, 2011, for European Patent Application No. 07795177.0, filed on May 21, 2007, 6 pages.
Final Office Action mailed on Aug. 23, 2010, for U.S. Appl. No. 11/609,838, filed Dec. 12, 2006, 20 pages.
Final Office Action mailed on Oct. 8, 2009, for U.S. Appl. No. 11/215,660, filed Aug. 29, 2005, 12 pages.

Final Office Action mailed on Mar. 22, 2011, for U.S. Appl. No. 11/828,835, filed Jul. 26, 2007, 11 pages.
Final Office Action mailed on Nov. 1, 2010, for U.S. Appl. No. 11/215,660, filed Aug. 29, 2005, 12 pages.
Final Office Action mailed on Apr. 29, 2011, for U.S. Appl. No. 11/751,605, filed May 21, 2007, 9 pages.
Final Office Action mailed on Aug. 3, 2011, for U.S. Appl. No. 11/736,438, filed Apr. 17, 2007, 11 pages.
International Search Report mailed on May 18, 2006, for PCT Patent Application No. PCT/US2005/045499, filed on Dec. 8, 2005, 4 pages.
International Search Report mailed on Sep. 28, 2007, for PCT Patent Application No. PCT/US2007/002096 filed on Jan. 23, 2007, 4 pages.
International Search Report mailed on Oct. 25, 2007, for PCT Patent Application No. PCT/US2007/003322, filed on Feb. 6, 2007, 5 pages.
International Search Report mailed on Oct. 26, 2007, for PCT Patent Application No. PCT/US2007/003631, filed on Feb. 9, 2007, 5 pages.
International Search Report mailed on Jan. 28, 2008, for PCT Patent Application No. PCT/US2007/012189, filed on May 21, 2007, 2 pages.
International Search Report mailed on Feb. 25, 2009, for PCT Patent Application No. PCT/US2008/071390, filed on Jul. 28, 2008, 2 pages.
International Search Report mailed on Mar. 13, 2009, for PCT Patent Application No. PCT/US2008/083034, filed on Nov. 10, 2008, 2 pages.
International Search Report mailed on Mar. 13, 2009, for PCT Patent Application No. PCT/US2008/079891, filed on Nov. 10, 2008, 2 pages.
International Search Report mailed on Apr. 6, 2009, for PCT Patent Application No. PCT/US2008/079878, filed on Oct. 14, 2008, 3 pages.
Invitation to Pay Additional Fees mailed on Dec. 29, 2008, for PCT Patent Application No. PCT/US2008/079891, filed on Oct. 14, 2008, 7 pages.
Japanese Office Action mailed on Jul. 19, 2011, for Japanese Patent Application No. 2007-550378, filed on Dec. 8, 2005, with English Translation, 11 pages.
Non-Final Office Action mailed on Jan. 10, 2008, for U.S. Appl. No. 11/160,646, filed Jul. 1, 2005, 6 pages.
Non-Final Office Action mailed on Mar. 12, 2008, for U.S. Appl. No. 11/153,007, filed Jun. 14, 2005, 11 pages.
Non-Final Office Action mailed on Mar. 25, 2009, for U.S. Appl. No. 11/215,660, filed Aug. 29, 2005, 11 pages.
Non-Final Office Action mailed on Mar. 29, 2010, for U.S. Appl. No. 11/215,660, filed Aug. 29, 2005, 16 pages.
Non-Final Office Action mailed on Apr. 6, 2010, for U.S. Appl. No. 11/609,838, filed Dec. 12, 2006, 25 pages.
Non-Final Office Action mailed on Aug. 24, 2010, for U.S. Appl. No. 11/834,540, filed Aug. 6, 2007, 11 pages.
Non-Final Office Action mailed on Oct. 18, 2010, for U.S. Appl. No. 11/626,189, filed Jan. 23, 2007, 11 pages.
Non-Final Office Action mailed on Oct. 28, 2010, for U.S. Appl. No. 11/828,835, filed Jul. 26, 2007, 11 pages.
Non-Final Office Action mailed on Dec. 22, 2010, for U.S. Appl. No. 11/751,605, filed May 21, 2007, 10 pages.
Non-Final Office Action mailed on Feb. 17, 2011, for U.S. Appl. No. 11/609,838, filed Dec. 12, 2006, 24 pages.
Non-Final Office Action mailed on Mar. 2, 2011, for U.S. Appl. No. 11/736,438, filed Apr. 17, 2007, 10 pages.
Non-Final Office Action mailed on May 23, 2011, for U.S. Appl. No. 12/101,050, filed Apr. 10, 2008, 11 pages.
Non-Final Office Action mailed on Jun. 28, 2011, for U.S. Appl. No. 11/938,256, filed Nov. 10, 2007, 23 pages.
Non-Final Office Action mailed on Aug. 4, 2011, for U.S. Appl. No. 11/609,838, filed Dec. 12, 2006, 16 pages.
Non-Final Office Action mailed on Aug. 15, 2011, for U.S. Appl. No. 11/626,189, filed Jan. 23, 2007, 13 pages.
Non-Final Office Action mailed on Sep. 9, 2011, for U.S. Appl. No. 11/751,596, filed May 21, 2007, 6 pages.
Non-Final Office Action mailed on Oct. 21, 2011, for PCT U.S. Appl. No. 12/251,406, filed Oct. 14, 2008, 8 pages.

Non-Final Office Action mailed on Oct. 26, 2011, for U.S. Appl. No. 11/673,470, filed Feb. 9, 2007, 40 pages.
Non-Final Office Action mailed on Nov. 23, 2011, for U.S. Appl. No. 11/672,020, filed Feb. 6, 2007, 12 pages.
Non-Final Office Action mailed on Feb. 13, 2012, for U.S. Appl. No. 13/275,206, filed Oct. 17, 2011, 13 pages.
Non-Final Office Action mailed on Feb. 14, 2012, for U.S. Appl. No. 12/251,383, filed Oct. 14, 2008, 9 pages.
Notice of Allowance mailed on Dec. 13, 2010, for U.S. Appl. No. 11/834,540, filed Aug. 6, 2007, 4 pages.
Notice of Allowance mailed on Jul. 22, 2011, for U.S. Appl. No. 12/101,050, filed Apr. 10, 2008, 7 pages.
Notice of Allowance mailed on Feb. 8, 2012, for U.S. Appl. No. 11/609,838, filed Dec. 12, 2006, 8 pages.
Preliminary Amendment filed Jan. 26, 2009, for U.S. Appl. No. 11/672,020, filed Feb. 6, 2007, 11 pages.
Response to European Communication filed Feb. 6, 2009, for European Patent Application No. 07777255.6, filed on May 21, 2007, 5 pages.
Response to European Office Action filed on Nov. 11, 2009, for European Patent Application No. 07783368.3, filed on Feb. 6, 2007, 12 pages.
Response to European Office Action filed on Jul. 7, 2010, for European Patent Application No. 06845440.4, filed on Dec. 13, 2006, 13 pages.
Response to European Office Action filed on Aug. 18, 2010, for European Patent Application No. 07717235.1, filed on Feb. 9, 2007, 7 pages.
Response to European Office Action filed on Mar. 8, 2011, for European Patent Application No. 05854262.2, filed on Dec. 8, 2005, 11 pages.
Response to European Office Action filed on Dec. 13, 2011, for European Patent Application No. 07795177.0, filed on May 21, 2007, 9 pages.
Response to Restriction Requirement filed on Jan. 26, 2009, for U.S. Appl. No. 11/215,660, filed Aug. 29, 2005, 2 pages.
Response to Restriction Requirement filed on Jul. 23, 2010, for U.S. Appl. No. 11/751,605, filed May 21, 2007, 9 pages.
Response to Restriction Requirement filed on Aug. 4, 2010, for U.S. Appl. No. 11/834,540, filed Aug. 6, 2007, 5 pages.
Response to Restriction Requirement filed on Sep. 9, 2010, for U.S. Appl. No. 11/626,189, filed Jan. 23, 2007, 8 pages.
Response to Restriction Requirement filed on Oct. 21, 2010, for U.S. Appl. No. 11/828,835, filed Jul. 26, 2007, 7 pages.
Response to Restriction Requirement filed on Feb. 8, 2011, for U.S. Appl. No. 11/736,438, filed Apr. 17, 2007, 8 pages.
Response to Restriction Requirement filed on Apr. 27, 2011, for U.S. Appl. No. 12/101,050, filed Apr. 10, 2008, 11 pages.
Response to Restriction Requirement filed on Jun. 16, 2011, for U.S. Appl. No. 11/751,596, filed May 21, 2007, 8 pages.
Response to Restriction Requirement filed on Oct. 31, 2011, for U.S. Appl. No. 11/672,020, filed Feb. 6, 2007, 3 pages.
Restriction Requirement mailed on Oct. 30, 2008, for U.S. Appl. No. 11/215,660, filed Aug. 29, 2005, 7 pages.
Restriction Requirement mailed on Jun. 25, 2010, for U.S. Appl. No. 11/751,605, filed May 21, 2007, 9 pages.
Restriction Requirement mailed on Jul. 13, 2010, for U.S. Appl. No. 11/834,540, filed Aug. 6, 2007, 8 pages.
Restriction Requirement mailed on Aug. 10, 2010, for U.S. Appl. No. 11/626,189, filed Jan. 23, 2007, 5 pages.
Restriction Requirement mailed on Sep. 21, 2010, for U.S. Appl. No. 11/828,835, filed Jul. 26, 2007, 6 pages.
Restriction Requirement mailed on Dec. 10, 2010, for U.S. Appl. No. 11/736,438, filed Apr. 17, 2007, 16 pages.
Restriction Requirement mailed on Mar. 11, 2011, for U.S. Appl. No. 12/101,050, filed Apr. 10, 2008, 6 pages.
Restriction Requirement mailed on Jun. 6, 2011, for U.S. Appl. No. 11/751,596, filed May 21, 2007, 6 pages.
Restriction Requirement mailed on Sep. 29, 2011, for U.S. Appl. No. 11/672,020, filed Feb. 6, 2007, 6 pages.
Restriction Requirement mailed on Nov. 28, 2011, for U.S. Appl. No. 12/251,383, filed Oct. 14, 2008, 6 pages.

Substitute Preliminary Amendment filed Mar. 8, 2010, for U.S. Appl. No. 11/672,020, filed Feb. 6, 2007, 2 pages.
Written Opinion of the International Searching Authority mailed on May 18, 2006, for PCT Patent Application No. PCT/US2005/045499, filed on Dec. 8, 2005, 9 pages.
Written Opinion of the International Searching Authority mailed on May 19, 2006, for PCT Patent Application No. PCT/US2005/044624, filed on Dec. 8, 2005, 8 pages.
Written Opinion of the International Searching Authority mailed on Jun. 20, 2007, for PCT Patent Application No. PCT/US2006/047748, filed on Dec. 13, 2006, 7 pages.
Written Opinion of the International Searching Authority mailed on Sep. 28, 2007, for PCT Patent Application No. PCT/US2007/002096 filed on Jan. 23, 2007, 8 pages.
Written Opinion of the International Searching Authority mailed on Oct. 25, 2007, for PCT Patent Application No. PCT/US2007/003322, filed on Feb. 6, 2007, 9 pages.
Written Opinion of the International Searching Authority mailed on Oct. 26, 2007, for PCT Patent Application No. PCT/US2007/003631, filed on Feb. 9, 2007, 7 pages.
Written Opinion of the International Searching Authority mailed on Dec. 11, 2007, for PCT Patent Application No. PCT/US2007/012358, filed on May 21, 2007, 6 pages.
Written Opinion of the International Searching Authority mailed on Jan. 28, 2008, for PCT Patent Application No. PCT/US2007/012189, filed on May 21, 2007, 7 pages.
Written Opinion of the International Searching Authority mailed on Oct. 23, 2008, for PCT Patent Application No. PCT/US2008/069435, filed on Jul. 8, 2008, 6 pages.
Written Opinion of the International Searching Authority mailed on Feb. 25, 2009, for PCT Patent Application No. PCT/US2008/071390, filed on Jul. 28, 2008, 7 pages.
Written Opinion of the International Searching Authority mailed on Mar. 13, 2009, for PCT Patent Application No. PCT/US2008/083034, filed on Nov. 10, 2008, 4 pages.
Written Opinion of International Searching Authority mailed on Mar. 13, 2009, for PCT Patent Application No. PCT/US2008/079891, filed on Nov. 10, 2008, 5 pages.
Written Opinion of International Searching Authority mailed on Apr. 6, 2009, for PCT Patent Application No. PCT/US2008/079878, filed on Oct. 14, 2008, 13 pages.
Amendment in Response to Non-Final Office Action filed on Dec. 16, 2011, for U.S. Appl. No. 11/938,256, filed Nov. 10, 2007, 10 pages.
Amendment in Response to Non-Final Office Action filed on Mar. 23, 2012, for U.S. Appl. No. 11/672,020, filed Feb. 6, 2007, 12 pages.
Japanese Office Action mailed Feb. 28, 2012, for Japanese Patent Application No. 2008-545817, filed on Dec. 13, 2006, with English Translation, 6 pages.
Japanese Office Action mailed on Feb. 28, 2012, for Japanese Patent Application No. 2008-551487, filed on Jan. 23, 2007, with English Translation, 9 pages.
Japanese Office Action mailed on Feb. 28, 2012, for Japanese Patent Application No. 2008-554410, filed on Feb. 9, 2007, with English Translation, 6 pages.
Japanese Office Action mailed on Mar. 6, 2012, for Japanese Patent Application No. 2008-553430, filed on Feb. 6, 2007, with English Translation, 6 pages.
Notice of Allowance mailed on Feb. 29, 2012, for U.S. Appl. No. 11/751,596, filed May 21, 2007, 10 pages.
Notice of Allowance mailed on Mar. 14, 2012, for U.S. Appl. No. 11/626,189, filed Jan. 23, 2007, 13 pages.

\* cited by examiner

DEVICE AND METHOD FOR REDUCING EFFECTS OF VIDEO ARTIFACTS

This application claims the benefit of U.S. Provisional Patent Application No. 60/801,748, filed May 19, 2006, the entire disclosure of which is incorporated herein by reference.

TECHNICAL FIELD OF THE INVENTION

The present invention relates to a device and method for reducing effects of video artifacts.

BACKGROUND OF THE INVENTION

Multiple endoscopic devices with multiple cameras and light sources may be used for medical procedures, inspection of small pipes, or remote monitoring. For example, such an endoscopic device may be a medical endoscope comprising a flexible tube, and a camera and a light source mounted on the distal end of the flexible tube. The endoscope is insertable into an internal body cavity through a body orifice to examine the body cavity and tissues for diagnosis. The tube of the endoscope has one or more longitudinal channels, through which an instrument can reach the body cavity to take samples of suspicious tissues or to perform other surgical procedures such as polypectomy.

There are many types of endoscopes, and they are named in relation to the organs or areas with which they are used. For example, gastroscopes are used for examination and treatment of the esophagus, stomach and duodenum; colonoscopes for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels.

Each endoscope has a single forward viewing camera mounted at the distal end of the flexible tube to transmit an image to an eyepiece or video camera at the proximal end. The camera is used to assist a medical professional in advancing the endoscope into a body cavity and looking for abnormalities. The camera provides the medical professional with a two-dimensional view from the distal end of the endoscope. To capture an image from a different angle or in a different portion, the endoscope must be repositioned or moved back and forth. Repositioning and movement of the endoscope prolongs the procedure and causes added discomfort, complications, and risks to the patient. Additionally, in an environment similar to the lower gastro-intestinal tract, flexures, tissue folds and unusual geometries of the organ may prevent the endoscope's camera from viewing all areas of the organ. The unseen area may cause a potentially malignant (cancerous) polyp to be missed.

This problem can be overcome by providing an auxiliary camera and an auxiliary light source. The auxiliary camera and light source can be oriented to face the main camera and light source, thus providing an image of areas not viewable by the endoscope's main camera. This arrangement of cameras and light sources can provide both front and rear views of an area or an abnormality. In the case of polypectomy where a polyp is excised by placing a wire loop around the base of the polyp, the camera arrangement allows better placement of the wire loop to minimize damage to the adjacent healthy tissue.

The two cameras may be based on different technologies and may have different characteristics. In many cases, the main camera is a charge coupled device (CCD) camera that requires a very intense light source for illumination. Such as a light source may be a fiber optic bundle. The auxiliary camera may be a complementary metal oxide semiconductor (CMOS) camera with a light emitting diode (LED) to provide illumination.

SUMMARY OF THE INVENTION

The inventors of the present application have observed that, when multiple imaging and light emitting devices are used as described in the background section of the present specification, artifacts may appear on the video images produced by the imaging devices. One example of the observed artifacts is a "thin line" near the top edge of a video image generated by a main endoscope's CCD imaging device, when the CCD imaging device is used in pair with retrograde imaging and light emitting devices.

The inventors believe that this "thin line" artifact is caused by how images are captured and/or processed by the CCD imaging device. Alternatively or additionally, the artifact may be related the video processing circuitry. In a CCD camera system, image data are captured and/or processed a single row of the image at a time. As a result, if there is a bright light source such as the retrograde light emitting device, individual pixels of the image can succumb to charge "leaks" which can spill over into the other light receptors in the same row. This may cause loss of portions of the video image and appearance of a "thin line" in the video image.

The present invention can be used to reduce the effects of the "thin line" artifact. In accordance with one aspect of the invention, an endoscopic system includes a first imaging device, a second imaging device, a light source, and a controller that reduces an artifact in an image produced by the first imaging device. In some embodiments, the first imaging device faces the light source.

In one preferred embodiment, the controller adjusts a frequency of the second imaging device's video clock signal so that a frequency of the second imaging device's video synchronization signal matches a frequency of the first imaging device's video synchronization signal.

In another preferred embodiment, the controller adjusts a phase of the second imaging device's video clock signal to vary the phase between the second imaging device's video synchronization signal and the first imaging device's video synchronization signal. The phase between the two video synchronization signals may be zero or nonzero.

In still another preferred embodiment, the controller synchronizes a duty cycle of the light source to turn on the light source only when the first imaging device is in a vertical blanking interval to reduce the size of the artifact.

In yet another preferred embodiment, the controller moves the artifact by adjusting a pulse width and/or delay timing of the light source. Preferably, the controller moves the artifact vertically.

In still yet another preferred embodiment, wherein the controller includes a phase lock loop circuit that is connected to the first imaging device to receive a video synchronization signal of the first imaging device and connected to the second imaging device to receive a video synchronization signal of the second imaging device and to send a video clock signal for the second imaging device, wherein the phase lock loop circuit adjusts a phase of the second imaging device's video clock signal so that a phase of the second imaging device's video synchronization signal matches a phase of the first imaging device's video synchronization signal.

In a further preferred embodiment, the phase lock loop circuit adjusts a frequency of the second imaging device's video clock signal so that a frequency of the second imaging device's video synchronization signal matches a frequency of the first imaging device's video synchronization signal.

In a still further preferred embodiment, the controller includes a light source driver, and the light source driver is connected to the phase lock loop circuit to receive the video clock signal. Preferably, the light source driver synchronizes a duty cycle of the light source to turn on the light source only when the first imaging device is in a vertical blanking interval to reduce the size of the artifact.

In a yet further preferred embodiment, the light source driver moves the artifact by adjusting a pulse width and/or delay timing of the light source. Preferably, the controller moves the artifact vertically.

In a still yet further preferred embodiment, the phase lock loop circuit includes a sync separator that is connected to the first imaging device to receive the video synchronization signal of the first imaging device and connected to the second imaging device to receive the video synchronization signal of the second imaging device. Preferably, the sync separator extracts a vertical synchronization signal from the video synchronization signal of the first imaging device and another vertical synchronization signal from the video synchronization signal of the second imaging device.

In another preferred embodiment, the phase lock loop circuit includes a phase detector that is connected to the sync separator to receive the vertical synchronization signals. Preferably, the phase detector computes the phase difference between the vertical synchronization signals using the vertical synchronization signal of the first imaging device as a reference signal.

In still another preferred embodiment, the phase lock loop circuit includes a low pass filter that is connected to the phase detector to receive the phase difference and that averages the phase difference to reduce the noise content of the phase difference.

In yet another preferred embodiment, the phase lock loop circuit includes an oscillator that is connected to the low pass filter to receive the averaged phase difference and that creates the video clock signal.

In accordance with another aspect of the invention, an endoscopic system includes a first imaging device, a second imaging device, a light source, and a controller that varies a phase difference between video synchronization signals of the first and second imaging devices to reduce an artifact in an image produced by the first imaging device.

In accordance with still another aspect of the invention, an endoscopic system includes a first imaging device, a first light source, a second imaging device, a second light source, and a controller. The first imaging device and light source may face the second imaging device and light source. Preferably, the controller includes a phase lock loop circuit that is connected to the first imaging device to receive a video synchronization signal of the first imaging device and connected to the second imaging device to receive a video synchronization signal of the second imaging device and to send a video clock signal for the second imaging device so that image frames of the imaging devices have the same frequency and are in phase. The first imaging device and light source may be powered on during one half of the frame period, and the second imaging device and light source are powered on during the other half of the frame period.

In a preferred embodiment, the frame frequency is sufficiently high such that eyes cannot sense that the first and second imaging devices and their light sources are intermittently powered on and off.

In accordance with a further aspect of the invention, a method for reducing an effect of a video artifact includes adjusting a phase of a second imaging device's video clock signal so that a phase of the second imaging device's video synchronization signal matches a phase of a first imaging device's video synchronization signal.

In a preferred embodiment, the method further includes adjusting a frequency of the second imaging device's video clock signal so that a frequency of the second imaging device's video synchronization signal matches a frequency of the first imaging device's video synchronization signal.

In another preferred embodiment, the method further includes synchronizing a duty cycle of a light source to turn on the light source only when the first imaging device is in a vertical blanking interval to reduce the size of the artifact, wherein the light source faces the first imaging device.

In yet another preferred embodiment, the method further includes moving the artifact by adjusting a pulse width and/or delay timing of the light source. Preferably, the moving step includes moving the artifact vertically.

In still yet another preferred embodiment, the adjusting step includes extracting a vertical synchronization signal from the video synchronization signal of the first imaging device and another vertical synchronization signal from the video synchronization signal of the second imaging device.

In a further preferred embodiment, the adjusting step includes computing the phase difference between the vertical synchronization signals using the vertical synchronization signal of the first imaging device as a reference signal.

In a still further preferred embodiment, the adjusting step includes averaging the phase difference to reduce the noise content of the phase difference.

In a yet further preferred embodiment, the adjusting step includes creating the video clock signal.

DETAILED DESCRIPTION OF EMBODIMENTS OF THE INVENTION

Figure 1:
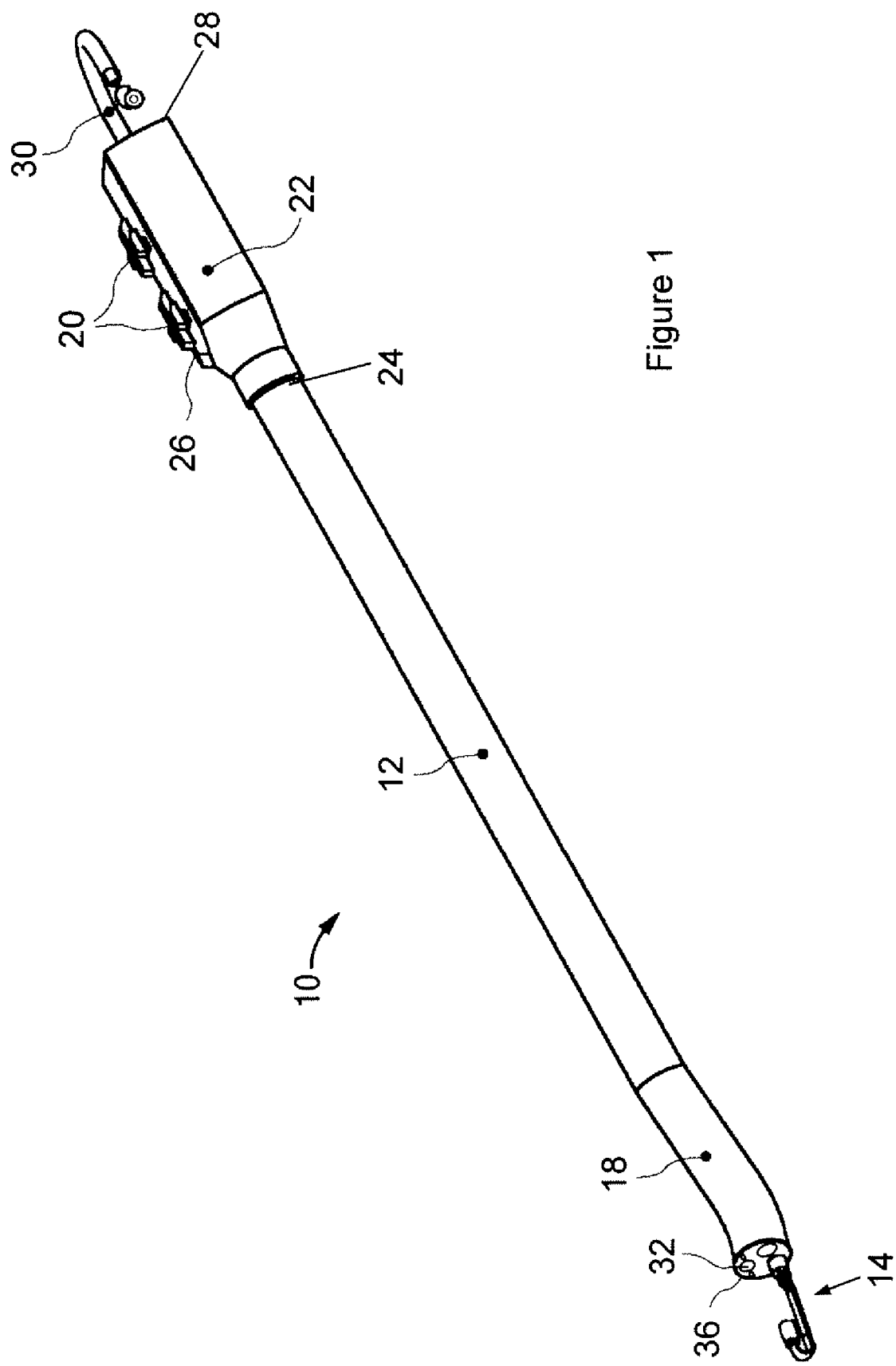
FIG. 1 shows a perspective view of an endoscope with an imaging assembly according to one embodiment of the present invention.

FIG. 1 illustrates an exemplary endoscope 10 of the present invention. This endoscope 10 can be used in a variety of medical procedures in which imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

Figure 2:
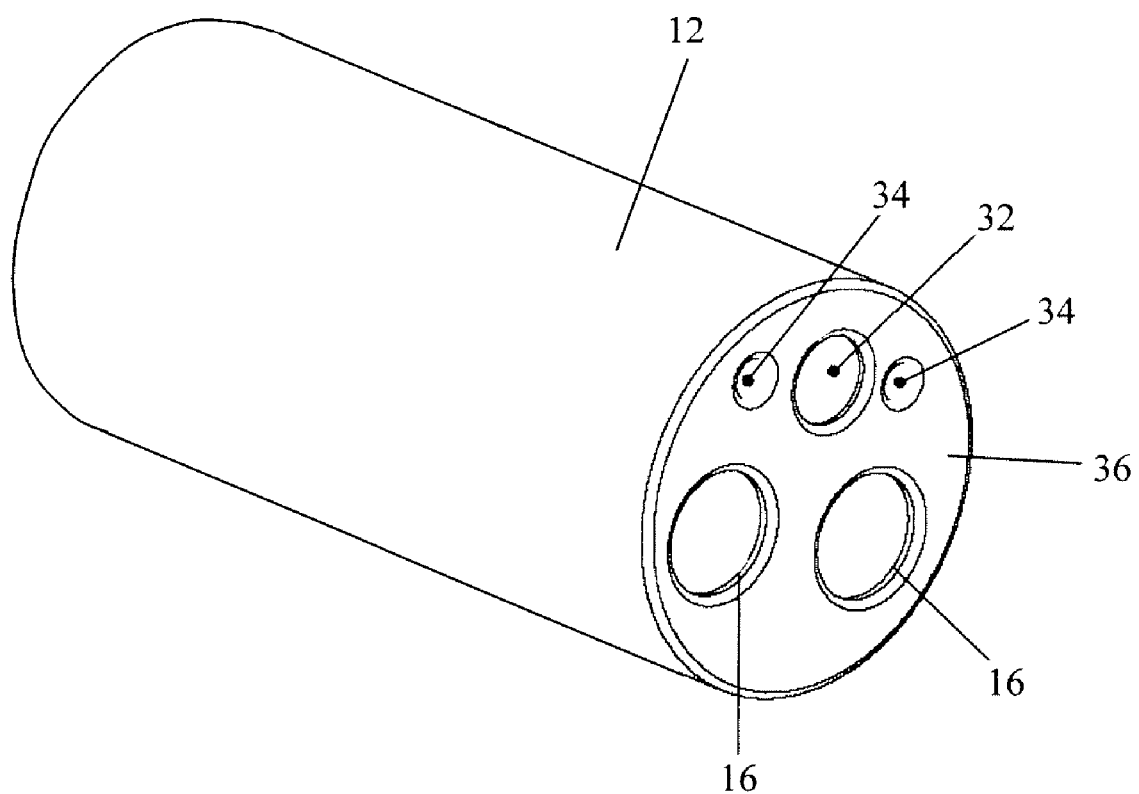
FIG. 2 shows a perspective view of the distal end of an insertion tube of the endoscope of FIG. 1.

The endoscope 10 of FIG. 1 includes an insertion tube 12 and an imaging assembly 14, a section of which is housed inside the insertion tube 12. As shown in FIG. 2, the insertion tube 12 has two longitudinal channels 16. In general, however, the insertion tube 12 may have any number of longitudinal channels. An instrument can reach the body cavity through one of the channels 16 to perform any desired procedures, such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels can be used to supply a washing liquid such as water for washing. Another or the same channel may be used to supply a gas, such as $CO_2$ or air into the organ. The channels 16 may also be used to extract fluids or inject fluids, such as a drug in a liquid carrier, into the body. Various biopsy, drug delivery, and other diagnostic and therapeutic devices may also be inserted via the channels 16 to perform specific functions.

The insertion tube 12 preferably is steerable or has a steerable distal end region 18 as shown in FIG. 1. The length of the distal end region 18 may be any suitable fraction of the length of the insertion tube 12, such as one half, one third, one fourth, one sixth, one tenth, or one twentieth. The insertion tube 12 may have control cables (not shown) for the manipulation of the insertion tube 12. Preferably, the control cables are symmetrically positioned within the insertion tube 12 and extend along the length of the insertion tube 12. The control cables may be anchored at or near the distal end 36 of the insertion tube 12. Each of the control cables may be a Bowden cable, which includes a wire contained in a flexible overlying hollow tube. The wires of the Bowden cables are attached to controls 20 in the handle 22. Using the controls 20, the wires can be pulled to bend the distal end region 18 of the insertion tube 12 in a given direction. The Bowden cables can be used to articulate the distal end region 18 of the insertion tube 12 in different directions.

As shown in FIG. 1, the endoscope 10 may also include a control handle 22 connected to the proximal end 24 of the insertion tube 12. Preferably, the control handle 22 has one or more ports and/or valves (not shown) for controlling access to the channels 16 of the insertion tube 12. The ports and/or valves can be air or water valves, suction valves, instrumentation ports, and suction/instrumentation ports. As shown in FIG. 1, the control handle 22 may additionally include buttons 26 for taking pictures with an imaging device on the insertion tube 12, the imaging assembly 14, or both. The proximal end 28 of the control handle 22 may include an accessory outlet 30 (FIG. 1) that provides fluid communication between the air, water and suction channels and the pumps and related accessories. The same outlet 30 or a different outlet can be used for electrical lines to light and imaging components at the distal end of the endoscope 10.

As shown in FIG. 2, the endoscope 10 may further include an imaging device 32 and light sources 34, both of which are disposed at the distal end 36 of the insertion tube 12. The imaging device 32 may include, for example, a lens, single chip sensor, multiple chip sensor or fiber optic implemented devices. The imaging device 32, in electrical communication with a processor and/or monitor, may provide still images or recorded or live video images. The light sources 34 preferably are equidistant from the imaging device 32 to provide even illumination. The intensity of each light source 34 can be adjusted to achieve optimum imaging. The circuits for the imaging device 32 and light sources 34 may be incorporated into a printed circuit board (PCB).

Figure 3:
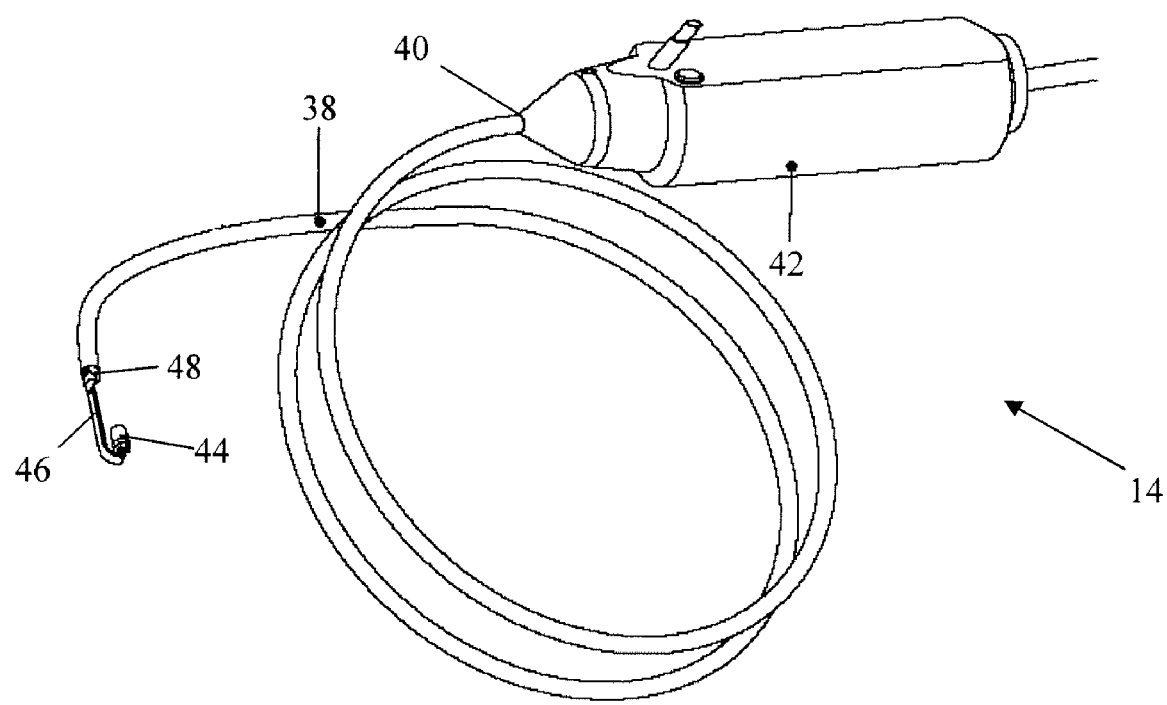
FIG. 3 shows a perspective view of the imaging assembly shown in FIG. 1.
Figure 4:
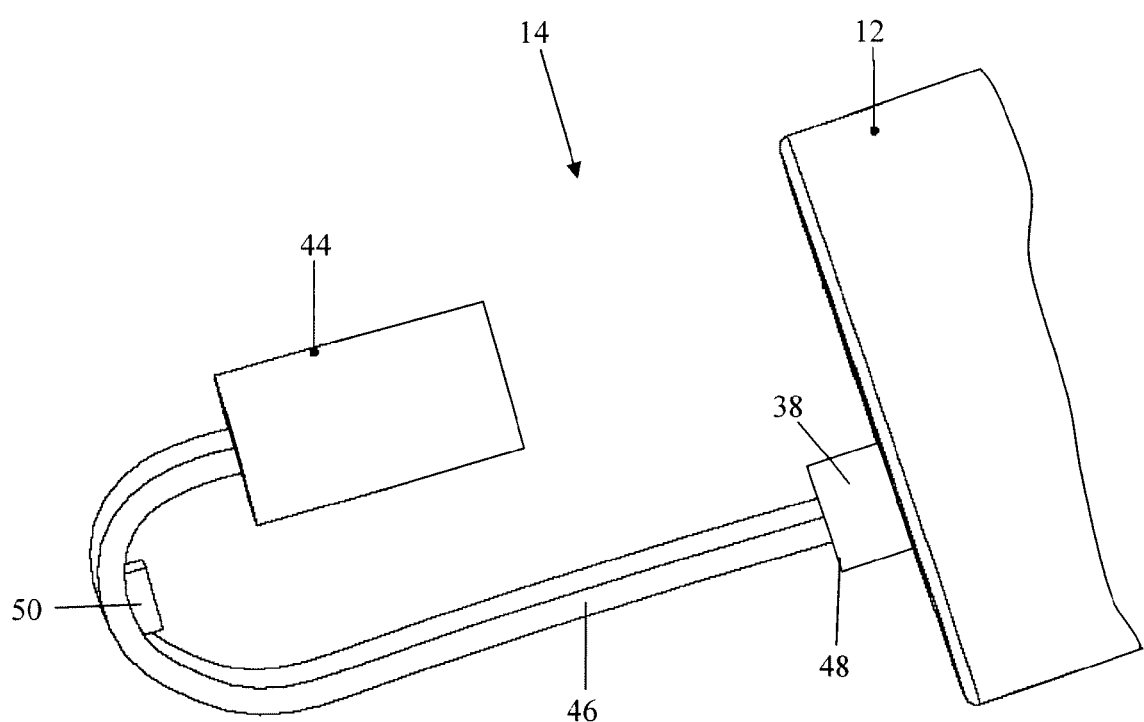
FIG. 4 shows a perspective view of the distal ends of the endoscope and imaging assembly of FIG. 1.

As shown in FIGS. 3 and 4, the imaging assembly 14 may include a tubular body 38, a handle 42 connected to the proximal end 40 of the tubular body 38, an auxiliary imaging device 44, a link 46 that provides physical and/or electrical connection between the auxiliary imaging device 44 to the distal end 48 of the tubular body 38, and an auxiliary light source 50 (FIG. 4). The auxiliary light source 50 may be an LED device.

As shown in FIG. 4, the imaging assembly 14 of the endoscope 10 is used to provide an auxiliary imaging device at the distal end of the insertion tube 12. To this end, the imaging assembly 14 is placed inside one of the channels 16 of the endoscope's insertion tube 12 with its auxiliary imaging device 44 disposed beyond the distal end 36 of the insertion tube 12. This can be accomplished by first inserting the distal end of the imaging assembly 14 into the insertion tube's channel 16 from the endoscope's handle 18 and then pushing the imaging assembly 14 further into the assembly 14 until the auxiliary imaging device 44 and link 46 of the imaging assembly 14 are positioned outside the distal end 36 of the insertion tube 12 as shown in FIG. 4.

Each of the main and auxiliary imaging devices 32, 44 may be an electronic device which converts light incident on photosensitive semiconductor elements into electrical signals. The imaging sensor may detect either color or black-and-white images. The signals from the imaging sensor can be digitized and used to reproduce an image that is incident on the imaging sensor. Two commonly used types of image sensors are Charge Coupled Devices (CCD) such as a VCC-5774 produced by Sanyo of Osaka, Japan and Complementary Metal Oxide Semiconductor (CMOS) camera chips such as an OVT 6910 produced by OnmiVision of Sunnyvale, Calif. Preferably, the main imaging device 32 is a CCD imaging device, and the auxiliary imaging device 44 is a CMOS imaging device.

When the imaging assembly 14 is properly installed in the insertion tube 12, the auxiliary imaging device 44 of the imaging assembly 14 preferably faces backwards towards the main imaging device 32 as illustrated in FIG. 4. The auxiliary imaging device 44 may be oriented so that the auxiliary imaging device 44 and the main imaging device 32 have adjacent or overlapping viewing areas. Alternatively, the auxiliary imaging device 44 may be oriented so that the auxiliary imaging device 44 and the main imaging device 32 simultaneously provide different views of the same area. Preferably, the auxiliary imaging device 44 provides a retrograde view of the area, while the main imaging device 32 provides a front view of the area. However, the auxiliary imaging device 44 could be oriented in other directions to provide other views, including views that are substantially parallel to the axis of the main imaging device 32.

Figure 5:
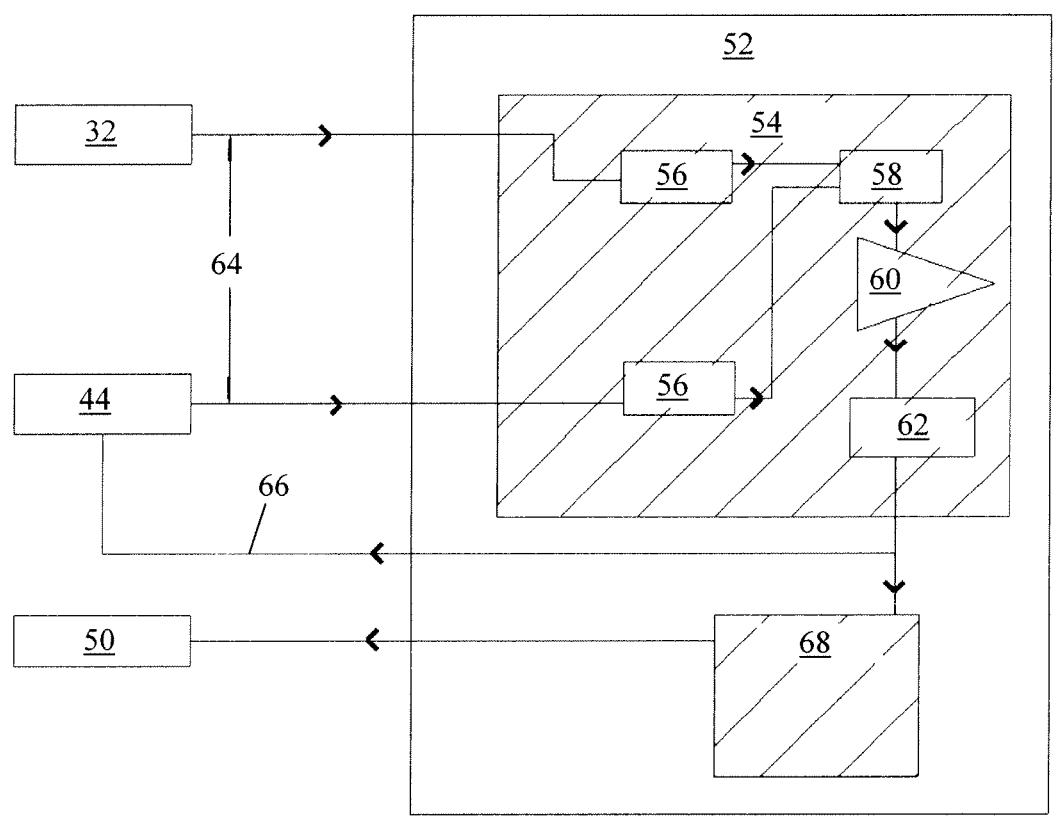
FIG. 5 shows a schematic diagram of a controller that, together with the endoscope of FIG. 1, forms an endoscope system.

As shown in FIG. 4, the link 46 connects the auxiliary imaging device 44 to the distal end 48 of the tubular body 38. Preferably, the link 46 is a flexible link that is at least partially made from a flexible shape memory material that substantially tends to return to its original shape after deformation. Shape memory materials are well known and include shape memory alloys and shape memory polymers. A suitable flexible shape memory material is a shape memory alloy such as nitinol. The flexible link 46 is straightened to allow the distal end of the imaging assembly 14 to be inserted into the proximal end of assembly 14 of the insertion tube 12 and then pushed towards the distal end 36 of the insertion tube 12. When the auxiliary imaging device 44 and flexible link 46 are pushed sufficiently out of the distal end 36 of the insertion tube 12, the flexible link 46 resumes its natural bent configuration as shown in FIG. 3. The natural configuration of the flexible link 46 is the configuration of the flexible link 46 when the flexible link 46 is not subject to any force or stress. When the flexible link 46 resumes its natural bent configuration, the auxiliary imaging device 44 faces substantially back towards the distal end 36 of the insertion tube 12 as shown in FIG. 5.

In the illustrated embodiment, the auxiliary light source 50 of the imaging assembly 14 is placed on the flexible link 46, in particular on the curved concave portion of the flexible link 46. The auxiliary light source 50 provides illumination for the auxiliary imaging device 44 and may face substantially the same direction as the auxiliary imaging device 44 as shown in FIG. 4.

The endoscope of the present invention, such as the endoscope 10 shown in FIG. 1, may be part of an endoscope system that also includes a controller. The term "controller" as used in this specification is broadly defined. In some embodiments, for example, the term "controller" may simply be a signal processing unit.

The controller can be used for, among others, reducing or eliminating the "thin line" artifacts described above. FIG. 5 illustrates a preferred embodiment 52 of the controller. The preferred controller 52 includes a phase lock loop (PLL) circuit 54. The PLL circuit 54 includes a sync separator 56, a phase detector 58, a low pass filter 60, and an oscillator 62.

The sync separator 56 is connected to each of the main and auxiliary imaging devices 32, 44 to receive a video synchronization signal 64 from each imaging device 32, 44. The sync separator 56 extracts a vertical synchronization signal from each video synchronization signal 64. The phase detector 58 is connected to the sync separator 56 and receives the vertical synchronization signals from the sync separator 56. The phase detector 56 then computes the phase difference between the vertical synchronization signals using the vertical synchronization signal of the main imaging device 32 as the reference signal. The low pass filter 60 is connected to the phase detector 58 and receives the phase difference from the phase detector 58. The low pass filter 60 averages the phase difference to reduce the noise content of the phase difference. The oscillator 62 is connected to the low pass filter 60 and receives the averaged phase difference. Based on the averaged phase difference, the oscillator 62 creates an output signal that matches the frequency and phase of the vertical synchronization signal of the main imaging device 32. This output signal of the PLL circuit 54 may be then amplified and sent to the auxiliary imaging device 44 as a video clock signal 66. This feedback control loop adjusts the phase and/or frequency of the auxiliary imaging device's video clock so that the phase and frequency of the auxiliary imaging device's video synchronization signal 64 match those of the main imaging device 32's video synchronization signal 64. In other words, the two imaging devices 32, 44 have the same frame frequency and frame phase.

The preferred controller 52 shown in FIG. 5 may also include an auxiliary light source driver 68 that is used to "pulse" the auxiliary light source 50. A "pulsed" light source is not constantly powered on. Instead, it is turned on and off intermittently at a certain frequency. The frequency, phase and duty cycle (pulse width) of the auxiliary light source 50 can be adjusted by the auxiliary light source driver 68. in addition, the output signal of the PLL circuit 54 may also be sent to the auxiliary light source driver 68 to match the frequency of the auxiliary light source 50 with that of the imaging devices 32, 44.

The inventors of the present application have discovered that the size and position of the artifact on an image produced by the main imaging device 32 may be adjusted by varying at least the duty cycle of the auxiliary light source 50 and by varying at least the phase of the auxiliary light source 50 relative to the imaging devices 32, 44. For example, the duty cycle of the auxiliary light source 50 may be adjusted to vary at least the size of the artifact. In particular, the size of the artifact may be reduced by decreasing the duty cycle of the auxiliary light source 50. In the case of the "thin line" artifact, the length of the artifact may be reduced by decreasing the duty cycle of the auxiliary light source 50.

For another example, the artifact on an image produced by the main imaging device 32 may be moved, such as vertically, by varying at least the phase of the auxiliary light source 50 relative to the imaging devices 32, 44. The controller 52 may allow a user to adjust the phase of the auxiliary light source 50 to move the artifact to a region of non-interest in the image such as the location of the auxiliary light source 50.

For a further example, the duty cycle and/or phase of the auxiliary light source 50 may be adjusted so that the auxiliary light source 50 is powered on only when the main imaging device 32 is in a vertical blanking interval, resulting in a reduction in the size of the artifact.

Similarly, using the above-described processes and devices, the size and/or position of an artifact on an image produced by the auxiliary imaging device 44 may be adjusted by varying at least the duty cycle of the main light source 34 and by varying at least the phase of the main light source 34 relative to the imaging devices 32, 44.

In addition, an artifact on an image produced by one of the image devices 32, 44 may also be minimized by introducing a phase difference between the video synchronization signals of the main and auxiliary imaging devices 32, 44 (i.e., introducing a phase delay between the frame rates of the two video signals). The PLL circuit 54 may be used to maintain the desired phase difference between the video synchronization signals. The controller 52 may be used to adjust the phase difference between the video synchronization signals to minimize the artifact.

The auxiliary imaging device 44 and its light source 50 may be connected to the controller 52 (not shown) via electrical conductors that extend from the imaging device 44 and light source 50; through the link 46, tubular body 38, and handle 42; to the controller 52. The electrical conductors may carry power and control commands to the auxiliary imaging device 44 and its light source 50 and image signals from the auxiliary imaging device 44 to the controller 52.

The controller 52 may be used to adjust the parameters of the imaging devices 32, 44 and their light sources 34, 50, such as brightness, exposure time and mode settings. The adjustment can be done by writing digital commands to specific registers controlling the parameters. The registers can be addressed by their unique addresses, and digital commands can be read from and written to the registers to change the various parameters. The controller 52 can change the register values by transmitting data commands to the registers.

In an alternate embodiment, the controller 52 may be used to reduce light interference between the main imaging device 32 and light source 34 and the auxiliary imaging device 44 and light source 50. Since the main imaging device 32 and light source 34 face the auxiliary imaging device 44 and light source 50, the main light source 34 interferes with the auxiliary imaging device 44, and the auxiliary light source 50 interferes with the main imaging device 32. Light interference is the result of the light from a light source being projected directly onto an imaging device. This may cause light glare, camera blooming, or over saturation of light, resulting in inferior image quality.

To reduce or eliminate light interference, the imaging devices 32, 44 and their light sources 34, 50 may be turned on and off alternately. In other words, when the main imaging device 32 and light source 34 are turned on, the auxiliary imaging device 44 and light source 50 are turned off. And when the main imaging device 32 and light sources 34 are turned off, the auxiliary imaging device 44 and light source 50 are turned on. Preferably, the imaging devices 32, 44 and their light sources 34, 50 are turned on and off at a sufficiently high frequency that eyes do not sense that the light sources 34, 50 are being turned on and off.

The timing of powering on and off the imaging devices 32, 44 and their light sources 34, 50 can be accomplished using the PLL circuit 54 shown in FIG. 5. The PLL circuit 54 may be employed to match the frame frequencies and phases of the imaging devices 32, 44 as discussed above. Then, the main imaging device 32 and light source 34 are powered on during one half of the frame period, and the auxiliary imaging device 44 and light source 50 are powered on during the other half of the frame period.

The above-described processes and devices may also be used when there are more than two imaging devices and two light sources and when the imaging devices and light sources are on two or more endoscopes.

The invention claimed is:

1. A controller configured for use with an endoscopic system, the controller comprising:
 a phase lock loop circuit that is configured to receive a video synchronization signal from a first imaging sensor and to receive a video synchronization signal from a second imaging sensor to generate a video clock signal to send to the second imaging sensor, wherein the video clock signal is generated such that image frames of the imaging sensors have the same fundamental frequency and are phase locked, and wherein the first imaging sensor and a first light source face the second imaging sensor and a second light source; and
 a light source driver adapted to be connected to the second light source, wherein the light source driver is further connected to the phase lock loop circuit to receive the video clock signal, and wherein the first imaging sensor and the first light source are configured to be activated during a first time interval, and wherein the second imaging sensor and second light source are configured to be activated during a second time interval that is distinct from the first time interval.

2. The controller of claim 1, wherein the controller is configured to lock a selected phase difference between the video clock signal and the first imaging sensor's video synchronization signal.

3. The controller of claim 1, wherein the light source driver is configured to drive the second light source for only a portion of a full duty cycle.

4. The controller of claim 1, wherein the light source driver is configured to adjust the location of an image artifact of the first imaging sensor by adjusting a phase difference between the video clock signal and the video synchronization signal of the first imaging sensor.

5. The controller of claim 1, wherein the light source driver is configured to decrease the duty cycle of the second light source to reduce the size of an image artifact of the first imaging sensor.

6. The sensor of claim 1, wherein the light source driver is configured to activate the second light source only when the first imaging sensor is in a vertical blanking interval.

7. An endoscopic system comprising:
 a first imaging sensor;
 a first light source;
 a second imaging sensor;
 a second light source, wherein the first imaging sensor and first light source face the second imaging sensor and second light source; and
 a controller including a phase lock loop circuit that is configured to receive a video synchronization signal from the first imaging sensor and to receive a video synchronization signal from the second imaging sensor to generate and adjust a video clock signal such that the second light source and the image frames of the first and second imaging sensors have the same fundamental frequency and are phase locked, wherein the first imaging sensor and first light source are activated during a first interval of the frame period, and wherein the second imaging sensor and second light source are activated during a second interval of the frame period that is distinct from the first interval.

8. The endoscopic system of claim 7, wherein a phase difference between the second imaging sensor's video synchronization signal and the first imaging sensor's video synchronization signal is not zero.

9. The endoscopic system of claim 7, wherein the controller is configured to adjust the location of an image artifact of the first image sensor.

10. The endoscopic system of claim 7, wherein the controller is configured to reduce the size of an image artifact of the first imaging sensor by decreasing the duty cycle of the second light source.

11. The endoscopic system of claim 7, wherein the second light source is activated only when the first imaging sensor is in a vertical blanking interval.

12. The endoscopic system of claim 7, wherein the controller further comprises
 a light source driver adapted to be connected to the second light source, wherein the light source driver is connected to the phase lock loop circuit to receive the video clock signal and configured to activate the second light source relative to the video clock signal.

13. The endoscopic system of claim 12, wherein the light source driver is configured to adjust the location of an image artifact of the first imaging sensor by adjusting a phase difference between the video clock signal and the video synchronization signal of the first imaging sensor.

14. The endoscopic system of claim 13, wherein the light source driver is configured to move the artifact vertically.

15. The endoscopic system of claim 12, wherein the light source driver is configured to reduce the size of an imaging artifact of the first imaging sensor by decreasing the duty cycle of the second light source.

16. The endoscopic system of claim 12, wherein the light source driver is configured to activate the second light source only when the first imaging sensor is in a vertical blanking interval.

17. The system of claim 7, wherein the frame frequency is sufficiently high such that eyes cannot sense that the first and second imaging sensors and their light sources are intermittently activated.

18. The endoscopic system of claim 7, wherein the controller is configured to lock a selected phase difference between the video clock signal and the video synchronization signal of the first imaging sensor.

19. The endoscopic system of claim 7, further comprising a light source driver, wherein the light source driver is connected to the phase lock loop circuit to receive the video clock signal.

20. The endoscopic system of claim 19, wherein the light source driver is configured to adjust the location of an image artifact of the first imaging sensor by adjusting a phase difference between the video clock signal and the video synchronization signal of the first imaging sensor.

21. The endoscopic system of claim 19, wherein the light source driver activates the second light source for only a portion of a full duty cycle.

22. The endoscopic system of claim 7, wherein the first light source is configured to be activated only when the first imaging sensor is acquiring an image, and wherein the second light source is configured to be activated only when the second imaging sensor is acquiring an image.

23. The endoscopic system of claim 7, wherein the controller is configured such that the first imaging sensor acquires an image and the first light source is activated during one half of the frame period, and wherein the second imaging sensor acquires an image and the second light source is activated during the other half of the frame period.

24. The endoscopic system of claim 19, wherein the light source driver is configured to reduce a size of an image artifact of the first imaging sensor by decreasing the duty cycle of the second light source.

25. A method for reducing light interference between a first imaging sensor and a second light source and a second imaging sensor and a first light source of an endoscopic system, wherein the first imaging sensor and the first light source face the second imaging sensor and the second light source, the method comprising:

using a phase lock loop circuit to receive a video synchronization signal from the first imaging sensor and to receive a video synchronization signal from the second imaging sensor and to generate and adjust a video clock signal for the second imaging sensor so that image frames of the first and second imaging sensors have the same fundamental frequency and are phase locked; and activating the first imaging sensor and first light source during a first interval of the frame period, and activating the second imaging sensor and second light source during a second interval of the frame period that is distinct from the first interval.

26. The method of claim 25, further comprising locking a selected phase difference between the video clock signal and the first imaging sensor's video synchronization signal.

27. The method of claim 25, further comprising adjusting the location of an image artifact of the first imaging sensor by adjusting a phase difference between the video clock signal and the video synchronization signal of the first imaging sensor.

28. The method of claim 27, wherein adjusting the phase difference moves the artifact vertically.

29. The method of claim 25, further comprising reducing the size of an image artifact of the first imaging sensor by decreasing the duty cycle of the second light source.

30. The method of claim 25, wherein the second light source is activated only when the first imaging sensor is in a vertical blanking interval.

* * * * *